(12) United States Patent
Boles et al.

(10) Patent No.: US 6,692,912 B1
(45) Date of Patent: Feb. 17, 2004

(54) NUCLEIC ACID-CONTAINING POLYMERIZABLE COMPLEX

(75) Inventors: T. Christian Boles, Waltham, MA (US); Stephen J. Kron, Oak Park, IL (US); Christopher P. Adams, Winter Hill, MA (US)

(73) Assignee: Matrix Technologies Corporation, Hudson, NH (US)

(*) Notice: Subject to any disclaimer, the term of this patent is extended or adjusted under 35 U.S.C. 154(b) by 0 days.

(21) Appl. No.: 09/550,817

(22) Filed: Apr. 18, 2000

Related U.S. Application Data

(60) Continuation of application No. 09/183,092, filed on Oct. 30, 1998, which is a division of application No. 08/812,105, filed on Mar. 5, 1997, now Pat. No. 5,932,711.

(51) Int. Cl.$^7$ ............................ C12Q 1/68; C07H 19/00; C07H 21/00; C07H 21/02; C07H 21/04
(52) U.S. Cl. ................ 435/6; 536/22.1; 536/23.1; 536/24.3; 536/25.3
(58) Field of Search ................... 435/6; 536/22.1, 536/23.1, 24.3, 25.3

(56) References Cited

U.S. PATENT DOCUMENTS

| | | | |
|---|---|---|---|
| 3,778,393 A | 12/1973 | Greber et al. | 260/17.45 G |
| 4,829,098 A | 5/1989 | Hoffman et al. | 522/5 |
| 5,034,428 A | 7/1991 | Hoffman et al. | 522/5 |
| 5,237,016 A | 8/1993 | Ghosh et al. | 525/329.4 |
| 5,453,461 A | 9/1995 | Helliger et al. | 525/54.1 |
| 5,478,893 A | 12/1995 | Ghosh et al. | 525/329.4 |
| 5,510,084 A | 4/1996 | Cros et al. | 422/104 |
| 5,663,242 A | 9/1997 | Ghosh et al. | 525/329.4 |

FOREIGN PATENT DOCUMENTS

| | | | |
|---|---|---|---|
| DE | 2003 266 | 8/1971 | |
| EP | 0 524 864 A1 | 1/1993 | |
| EP | 06121698 | 5/1994 | |
| JP | H3[1991]-47097 | 2/1991 | |
| JP | 06121698 | 6/1994 | C12Q/1/68 |
| WO | WO92/07882 * | 5/1992 | |
| WO | WO 92/20702 * | 11/1992 | C07K/5/00 |
| WO | WO 97/45721 | 12/1997 | |

OTHER PUBLICATIONS

Acevedo et al. "Synthesis of propane–2,3–diol combinatorial monomers" Tetrahedron Letters vol. 37, No: 23, pp. 3931–3934, 1996.*

Y. Ozaki et al., "Affinity capillary electrophoresis using DNA conjugates"; Nucleic Acids Symposium Series No. 37:235–236, 1997.

S. Nagahara et al., "Hydrogel formation via hybridization oligonucleotides derivatized in water–soluble vinyl polymers"; Polymer Gels and Networks, 4: 111–127 [1996].

L. Dong et al., "A New Method for Immobilization of Biomolecules Using Preirradiation Grafting at Low Temperature"; Radiat. Phys. Chem. vol. 26 No. 2:177–182 [1986].

Lamture et al., Direct detection of nucleic acid hybridization on the surface of a charge coupled device, *Nucleic Acids Research* 22: 2121 (1994).

Caruther et al., Chemical synthesis of deoxyoligonucleotides by the phosphoramidite method, *Methods in Enzymology* 154: 230 (1985).

Shumaker et al., Mutation detection by solid phase primer extension, *Hum. Mutat.* 7: 346 (1996).

Southern, DNA chips: analysing sequence by hybridization to oligonucleotides on a large scale, *Trends in Genetics* 12: 110 (1996).

Sandler and Karo, *Polymer Synthesis 1*: Chapters 10 and 12 (1992).

Livache et al., *Nucleic Acids Research* 22: 2915–2921 (1994).

* cited by examiner

*Primary Examiner*—Jezia Riley
(74) *Attorney, Agent, or Firm*—Wood, Herron & Evans, L.L.P.

(57) ABSTRACT

Disclosed is a polymerizable complex containing a covalently attached nucleic acid molecule which, under appropriate conditions, is capable of copolymerization with a second polymerizable ethylene-containing monomer unit to form a polymerized layer. The polymerized layer containing attached nucleic acid is useful in a variety of contexts including, for example, hybridization assays. The polymerized layer containing the covalently attached nucleic acid molecule can be formed into a variety of shapes, or attached to a formed material through appropriate chemistry.

35 Claims, No Drawings

SEQUENCE LISTING

<160> NUMBER OF SEQ ID NOS: 3

<210> SEQ ID NO 1
<211> LENGTH: 38
<212> TYPE: DNA
<213> ORGANISM: Artificial Sequence
<220> FEATURE:
<223> OTHER INFORMATION: Synthetic construct

<400> SEQUENCE: 1
tttttttttc gggatcccag gcccgggaac gtattcac            38

<210> SEQ ID NO 2
<211> LENGTH: 20
<212> TYPE: DNA
<213> ORGANISM: Artificial Sequence
<220> FEATURE:
<223> OTHER INFORMATION: synthetic construct

<400> SEQUENCE: 2
gtgaatacgt tcccgggcct            20

<210> SEQ ID NO 3
<211> LENGTH: 18
<212> TYPE: DNA
<213> ORGANISM: Artificial Sequence
<220> FEATURE:
<223> OTHER INFORMATION: synthetic sequence

<400> SEQUENCE: 3
tgaacgtgga tgaagttg            18

NUCLEIC ACID-CONTAINING POLYMERIZABLE COMPLEX

This application is a continuation of U.S. application Ser. No. 09/183,092, filed Oct. 30, 1998, which is a divisional of U.S. application Ser. No. 08/812,105, filed Mar. 5, 1997, now U.S. Pat. No. 5,932,711.

BACKGROUND OF THE INVENTION

Various methods have been developed to analyze nucleic acid molecules present in experimental or diagnostic samples. Many of these techniques are assays wherein the sample is placed in contact with a solid support. The solid support contains nucleic acid molecules which have been immobilized by covalent or noncovalent attachment. Immobilization of a nucleic acid molecule to a spatially defined position on a solid support can be used in many ways. These uses include: hybridization assays which are able to identify an individual nucleic acid of interest present in an experimental or diagnostic sample containing multiple unique nucleic acids (Southern, *Trends in Genetics* 12:110–115 (1996)); hybridization assays which are able to identify genes which have a mutation such that the gene present in the experimental or diagnostic sample differs from that of the wild-type gene (Southern, WO 89/10977 (1989)); and in polymerase extension assays where the immobilized nucleic acids serve as primers for DNA synthesis by a DNA polymerase enzyme following hybridization to complementary target nucleic acids that may be present in the sample (Shumaker et al., *Hum. Mut.* 7:346–354 (1996); Syvanen et al., *Am. J. Hum. Genet.* 52:46–59 (1993)).

Presently, there are a number of known methods for covalently coupling a nucleic acid to a solid support for use in an experimental or diagnostic assay. These can be divided into two categories: 1) those in which preformed nucleic acids are coupled to the support; and 2) those in which the nucleic acids are synthesized in situ on the support.

In the first approach, the nucleic acids are deposited on the support either by hand or by automated liquid handling equipment (Lamture et al., *Nucleic Acids Research* 22:2121–2125 (1994); Yershov et al., *Proc. Natl. Acad. Sci. USA* 93:4913–4918 (1996)). To effect covalent attachment of the nucleic acids to the support, either the support, the nucleic acids, or both, are chemically activated prior to deposition. Alternatively, the nucleic acids can be deposited on the support and nonspecifically immobilized by physical means such as heat or irradiation with ultraviolet light (Life Science Research Product Catalog, BioRad Laboratories, Richmond, Calif., pg.269–273 (1996); Meinkoth and Wahl, *Analytical Biochemistry* 138:267–284 (1984)). In general, chemically mediated coupling is preferred since specific, well defined attachments can be accomplished, thereby minimizing the risk of unwanted artifacts from the immobilization process.

In the second approach, oligonucleotides are synthesized directly on the support using chemical methods based on those used for solid phase nucleic acid synthesis (Southern et al., *Nucleic Acids Research* 22:1368–1373 (1994)). Recently, specialized apparatus and photolithographic methods have been introduced which allow the synthesis of many different oligonucleotides at discrete, well-defined positions on planar glass or silica supports (Pease et al., *Proc. Natl Acad. Sci. USA* 91:5022–5026 (1994)). In general, these methods are most useful for applications which require many hundreds or thousands of different immobilized nucleic acids, such as sequencing by hybridization.

Yet another method presently in use to couple a nucleic acid molecule to a solid support involves the formation of an electroconducting conjugated polymerized layer (Livache et al., *Nucleic Acids Research* 22:2915–2921 (1994)). This polymerized layer is formed by copolymerization of a mixture containing pyrrole monomers and oligonucleotides covalently linked to a pyrrole monomer. The copolymerization reaction initiates following application of an electrical charge through the electrode which has been placed into the mixture containing the copolymerizable components. The dimensions of the polymerized layer which coats the surface of the electrode can be varied by adjusting the surface area of the electrode which is placed into the mixture.

Each of the methods disclosed above have specific limitations. For instance, the polymerized layer which coats the surface of an electrode can not be formed on a solid support which is not able to transmit an electrical charge into the mixture containing the copolymerizable monomer units. Most of the other disclosed methods are also limited to solid supports of a particular type. In addition, several of these methods require special types of equipment, and involve a degree of technical difficulty which may make it difficult to covalently link a nucleic acid molecule to a solid support in a reproducible manner.

SUMMARY OF THE INVENTION

The invention relates in one aspect to a polymerizable complex comprising a nucleic acid molecule which is derivatized by attachment to a first polymerizable ethylene-containing monomer unit which, under appropriate conditions, is capable of copolymerization with a second polymerizable ethylene-containing monomer unit. The copolymerization produces a polymerized layer which contains the covalently linked nucleic acid molecule. The nucleic acid molecule is attached to the first polymerizable ethylene-containing monomer unit either directly or through a chemical linker group.

In another aspect, the present invention relates to a β-cyanoethyl phosphoramidite reagent comprising:

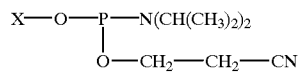

wherein X contains either a polymerizable ethylene-containing monomer unit, or a chemically protected version of same which can be deprotected using appropriate techniques.

In a further aspect, the present invention relates to a β-cyanoethyl phosphoramidite reagent comprising:

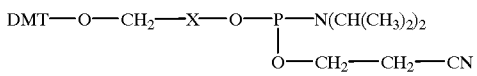

wherein X contains either a polymerizable ethylene-containing monomer unit, or a chemically protected version of same which can be deprotected using appropriate techniques, and DMT is a 4,4'-dimethoxytrityl group.

The invention relates in another aspect to a support for oligonucleotide synthesis having the general structure:

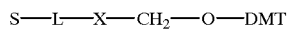

wherein S is a solid support material and L is a linker group. The linker group is cleavable by appropriate means at the end of oligonucleotide synthesis to release the completed oligonucleotide product. X contains either a polymerizable ethylene-containing monomer unit or a chemically protected version of same, which can be deprotected using appropriate techniques, and DMT is a 4,4'-dimethoxytrityl group.

In another aspect, the present invention relates to a support for oligonucleotide synthesis having the general structure:

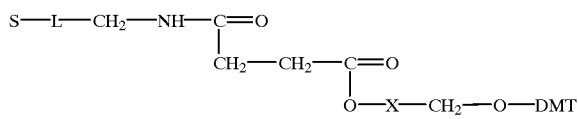

wherein S is a support material, L is a linker group, and X contains either a polymerizable ethylene-containing monomer unit, or a chemically protected version of same which can be deprotected using appropriate techniques, and DMT is a 4,4'-dimethoxytrity group.

In a further aspect of the present invention, the first and second polymerizable ethylene-containing monomer units are selected from the group consisting of monosubstituted ethylenes of general structure $CH_2$=CHX, or unsymmetrically (1,1-) disubstituted ethylenes of the general structure $CH_2$=CXY. In preferred embodiments of the invention, the first polymerizable ethylene-containing monomer unit is a derivative of acrylamide, methacrylamide, acrylic acid, or methacrylic acid.

The present invention further relates to a polymerized composition which is produced by a method comprising incubating a polymerizable complex and at least one second polymerizable ethylene-containing monomer unit under conditions appropriate for polymerization. The first and second polymerizable ethylene groups are selected from the group consisting of monosubstituted ethylenes of general structure CH2=CHX, or unsymmetrically (1,1-) disubstituted ethylenes of the general structure CH2=CXY.

In another aspect, the present invention relates to a method for producing a polymerized composition by incubating a polymerizable complex and at least one second polymerizable ethylene-containing monomer unit under conditions appropriate for polymerization. The first and second polymerizable ethylene groups are selected from the group consisting of monosubstituted ethylenes of general structure CH2=CHX, and unsymmetrically (1,1-) disubstituted ethylenes of the general structure CH2=CXY.

In a further aspect, the present invention relates to a composition comprising a formed material which is linked covalently to a nucleic acid-containing a polymerized coating layer, produced by providing a formed material bearing ethylene groups on an exposed surface. Under appropriate polymerization conditions, the formed material bearing exposed polymerizable ethylene groups is contacted with a solution comprising the polymerizable nucleic acid complex and at least one second polymerizable ethylene-containing monomer unit with which the polymerizable nucleic acid complex is capable of copolymerizing.

The invention also relates to a method for producing a composition comprising a formed material which is linked covalently to a nucleic acid-containing polymerized coating layer. The method comprises providing a formed material bearing polymerizable ethylene groups on an exposed surface. The exposed surface of the formed material is contacted with a solution comprising a polymerizable complex, said polymerizable complex being capable of copolymerization in the presence of at least one second polymerizable ethylene-containing monomer unit under appropriate conditions. The first and second polymerizable ethylene-containing monomer units are selected from the group consisting of monosubstituted ethylenes of general structure CH2=CHX, and unsymmetrically (1,1-) disubstituted ethylenes of the general structure CH2=CXY.

DETAILED DESCRIPTION OF THE INVENTION

The present invention is based on the development of a polymerizable complex comprised of a first polymerizable ethylene-containing monomer unit covalently linked to a nucleic acid molecule. The preferred polymerizable ethylene-containing monomer units include derivatives of acrylamide, methacrylamide, acrylic acid, methacrylic acid and structurally related amides and esters thereof. In general, these monomer units are widely commercially available, easy to polymerize using standard chemical procedures, and most are water soluble (Sandler and Karo, *Polymer Synthesis* Vol. 1, Ch. 10 and 12, Academic Press, Inc. (1992); Sandler and Karo, *Polymer Synthesis* Vol. 2, Ch. 9, Academic Press, Inc. (1994)).

The attachment of the first polymerizable ethylene-containing monomer unit to the nucleic acid to form a polymerizable complex can be direct or indirect. If indirect, the attachment is made through a chemical linker group. Direct coupling involves the linkage of the first polymerizable ethylene-containing monomer unit to the nucleic acid without the use of a linker. For many hybridization or polymerase extension assays, indirect attachment using a hydrophilic chemical linker group is preferred, in order to reduce steric hindrance between the immobilized nucleic acid and the support.

When the modified first polymerizable ethylene-containing monomer unit is mixed with a second unmodified polymerizable ethylene-containing monomer unit which is not attached to a nucleic acid molecule and a chemical polymerization initiator, the resultant polymerization reaction yields a polymerized layer to which the nucleic acid is covalently attached. A polymerized layer formed in this manner consists of an interwoven network of linear polymer chains.

To form a polymerized layer with more mechanical strength and durability, a cross-linking reagent, comprised of a multifunctional monomer unit containing two or more polymerizable ethylene-containing monomer units can be added to the polymerization reaction as taught in the prior art (Sandler and Karo, *Polymer Synthesis* Vol. 1, Ch. 10 and 12, Academic Press, Inc. (1992); Sandler and Karo, *Polymer Synthesis* Vol. 2, Ch. 9, Academic Press, Inc. (1994)). Preferred cross-linking reagents include the bis-acrylates, N,N' methylene(bis)acrylamide and ethylene glycol dimethacrylate.

The polymerized layer acts as a solid matrix which anchors the nucleic acid molecules to a defined locus and allows the nucleic acid molecules to be conveniently used in various experimental and diagnostic techniques. The polymerized layer may be deposited in a number of shapes. These include spots, strips, cylinders, uniform planar layers, beads as well as other shapes not disclosed above depending on the needs of the specific assay. When creating a polymerized layer, there is no restriction on the number of unique polymerizable ethylene-containing monomer units that can be used. In practice, more than one unique first modified (i.e., modified by attachment to a nucleic acid molecule) and more than one unique second unmodified polymerizable ethylene-containing monomer unit can be mixed with a chemical polymerizing initiator to form the polymerized layer provided that each species participates in the copolymerization. However, in preferred embodiments, the polymerized layer will be formed from a mixture containing one or two unique first modified polymerizable ethylene-containing monomer units, one unique second unmodified polymerizable ethylene-containing monomer unit, and a cross-linking reagent.

Examples of experimental or diagnostic methods for which the present invention is applicable include the detection and capture of a nucleic acid sequence of interest from an experimental or clinical sample, and primer extension assays to detect or amplify a predetermined nucleic acid sequence. As discussed, the polymerized layer can be produced in a variety of embodiments depending upon the intended application.

In the present invention, as stated above, the first polymerizable ethylene-containing monomer unit is covalently attached to a nucleic acid molecule. Described below are several examples of nucleic acid molecules which can be effectively coupled to the first polymerizable ethylene-containing monomer units. For example, the covalently attached nucleic acid molecule can be a deoxyribonucleic acid (DNA) molecule. All types of modified DNA which contain an appropriate chemical functionality can be attached to the first polymerizable ethylene-containing monomer units. These include, for example, fragments of genomic DNA, portions of a cDNA, PCR amplified DNA molecules or synthetic oligonucleotides.

Both double and single-stranded nucleic acids can be immobilized using the present invention. For applications that require nucleic acid hybridization, immobilized single stranded nucleic acids will be preferred. However, double-stranded nucleic acids can also be immobilized using the present invention, and may be useful for other applications. For instance, immobilized double-stranded DNA probes would be useful to screen for sequence-specific DNA binding agents that recognize double-stranded DNA, such as transcriptional regulatory proteins or triplex-forming nucleic acids.

In addition to the presence of functional chemical groups, a variety of additional issues are considered when selecting a DNA molecule for attachment to the polymerizable ethylene-containing monomer units. One such issue is the length of the DNA molecule. For experimental or diagnostic assays which rely on hybridization, the DNA molecule which is covalently attached to the polymerized layer should be long enough to allow hybridization to nucleic acid molecules contained in an experimental or diagnostic sample. However, the DNA molecule which is attached to the polymerized layer should be short enough that it will not adopt secondary or tertiary structures which inhibit its use as an experimental or diagnostic tool. Therefore, for several significant applications the preferred DNA molecule is an oligonucleotide. The preferred size of oligonucleotides which are covalently attached to an ethylene-containing monomer unit can vary. However, oligonucleotides having a size which is in the range of 5–50 nucleotides are particularly convenient since they are easy to synthesize chemically, and are water soluble even at high concentrations. An additional advantage offered by oligonucleotides is the high degree of stability exhibited by oligonucleotides in assays which require high stringency conditions. It should be noted that although oligonucleotides are convenient for use in connection with a variety of applications, there is no inherent upper limit on the size of the DNA molecule which can be attached to the first polymerizable ethylene-containing monomer unit. For some applications, the use of high molecular weight DNA molecules may offer advantages over oligonucleotides.

Another type of nucleic acid molecule which can be covalently attached to a first polymerizable ethylene-containing monomer unit is a ribonucleic acid (RNA) molecule. As discussed above, with regard to the size of the DNA molecule to be utilized, the preferred RNA molecule is one which is long enough to interact with the target nucleic acid but short enough such that secondary or tertiary structures which could prevent the interaction of the RNA molecule with a target nucleic acid molecule in an experimental or diagnostic sample do not form.

The size of the RNA molecule which is used will depend on the requirements of a particular experimental or diagnostic assay. For instance, for many hybridization assays, the preferred size of RNA molecules will range from 5–50 bases, while in other assays, high molecular weight RNA molecules of several hundred base pairs may be appropriate. Unlike DNA, the use of RNA requires special precautionary handling procedures due to the liability of RNA. At a minimum this requires specially prepared buffers and samples which have been treated to remove RNAse activity. However, complementary RNA-RNA and RNA-DNA duplexes have greater thermal stability than DNA-DNA duplexes, and RNA containing duplexes can be processed by different enzymes than DNA-DNA duplexes. These special properties may be exploited for selective hybridizations and analysis of RNA targets. Therefore, assays using immobilized RNA probes may be useful for RNA-based experimental and diagnostic tests.

While DNA oligonucleotides containing the four standard deoxynucleotides are most frequently used in assays which incorporate immobilized probes, probes containing modified nucleotides may also be useful. For instance, nucleotides containing deazaguanine and uracil bases may be used in place of guanine and thymine-containing nucleotides to decrease the thermal stability of hybridized probes (Wetmur, *Critical Reviews in Biochemistry and Molecular Biology*26:227–259 (1991)). Similarly, 5-methylcytosine can be substituted for cytosine if hybrids of increased thermal stability are desired (Wetmur, *Critical Reviews in Biochemistry and Molecular Biology*26:227–259 (1991)). Modifications to the ribose sugar group, such as the addition of 2'-O-methyl groups can reduce the nuclease susceptibility of immobilized RNA probes (Wagner, *Nature* 372:333–335 (1994)). Modifications that remove negative charge from the phosphodiester backbone can increase the thermal stability of hybrids (Moody et al., *Nucleic Acids Research* 17:4769–4782 (1989). It is also possible to synthesize oligonucleotides which contain non-purine, non-pyrimidine base analogues which may be useful for specialized applications (Glen Research Catalog, Glen Research, Sterling, Va., pg. 25 (1996)).

Nucleic acid analogues can also be useful as immobilized probes. An example of a useful nucleic acid analogue is the peptide nucleic acid (PNA), in which standard DNA bases are attached to a modified peptide backbone comprised of repeating N-(2-aminoethyl)glycine units (Nielsen et al., *Science* 254:1497–1500 (1991)). The peptide backbone is capable of holding the bases at the proper distance to facilitate hybridization with conventional DNA and RNA single strands. PNA-DNA hybrid duplexes are much stronger than otherwise equivalent DNA-DNA duplexes, probably due to the fact that there are no negatively charged phosphodiester linkages in the PNA strand. In addition, because of their unusual structure, PNAs are very resistant to nuclease degradation. For these reasons, PNA analogues are useful for immobilized probe assays. It will be apparent to those of skill in the art that similar modified backbone design strategies can be used to construct other nucleic acid analogues that will exhibit useful properties for immobilized probe assays.

The nucleic acid may be covalently attached to the first polymerizable ethylene-containing monomer unit directly, or it may be attached via a chemical linker group. In the present invention, a linker is the chemical constituent which is covalently attached at one point to the first polymerizable ethylene-containing monomer unit and covalently attached at a second point to the nucleic acid molecule. The result is that the first polymerizable ethylene-containing monomer unit is covalently attached to the linker which is covalently attached to the nucleic acid molecule, thereby forming a polymerizable complex. For many applications, the incorporation of a linker group will be preferred to avoid steric interference from the support in hybridization or polymerase extension reactions utilizing the immobilized probe. However, there may be other assays in which close proximity to the support surface may be beneficial and a linker would reduce efficiency. In these cases, direct coupling of the first polymerizable ethylene-containing monomer unit to the nucleic acid may be more useful.

The linker itself can consist of many different components, each having a characteristic property offering a unique advantage. One skilled in the art of organic synthesis could design and synthesize a great variety of linkers having the required chemical functionality to join the nucleic acid to the first polymerizable ethylene-containing monomer unit. Examples of different linkers which can be used in the present invention include, for example: peptide chains, carbohydrate chains, poly(ethylene glycol), poly(vinyl alcohol), and poly(vinyl pyrrolidone). This listing is by no means comprehensive, a wide array of appropriate linkers can be designed and synthesized through the application of routine experimentation (Sandler and Karo, *Polymer Synthesis* Vol. 1, Academic Press, Inc. (1992); Sandler and Karo, *Polymer Synthesis* Vol. 2, Academic Press, Inc. (1994)).

For application to hybridization and polymerase extension assays, the preferred linker should be hydrophilic, and have the capability to extend out into an aqueous solution and away from the polymer layer. The length of the linker can vary, but a longer linker is preferable since such a linker will increase the distance between the nucleic acid and the polymerized layer, thereby reducing inhibition of hybridization due to steric factors. As mentioned previously, when selecting a particular linker, the length should be chosen such that the tendency to form secondary and tertiary structures is minimized.

Again, for application in hybridization contexts, the linker should not be highly negatively charged. A linker which has a negative charge is likely to repel a nucleic acid molecule since the nucleic acid molecule itself exhibits a highly negative charge. Among other considerations is the polarity of the linker. In general, polar linkers should provide better probe accessibility in aqueous assays. For use in hybridization contexts, the chemical bond between the linker and the probe should be strong enough to survive harsh conditions, for example, exposure to highly basic denaturing conditions. The bond should also be thermally stable, with the capability to survive prolonged exposure to both high and low temperatures. Finally (for most applications), once the polymerizable complex is formed, the linker should not be chemically reactive with the nucleic acid molecule, the polymerizable ethylene-containing monomer unit, or the experimental or diagnostic sample which is to be tested.

An example of a linker which meets the criteria described above is polyethylene glycol ($CH_2$—$CH_2$—O), also known as PEG. In a preferred embodiment, PEG is capable of forming long chains consisting of between 1 and 10,000 covalently attached repeats of the monomer unit ($CH_2$—$CH_2$—O). However, chains longer than 10,000 repeating monomers can also be prepared. These PEG chains are hydrophilic, stable under harsh conditions and non-reactive with any of the other components of the polymerizable complex or target molecules present in experimental or diagnostic samples.

In some instances, an assay may require a linker which can be cleaved to release the nucleic acid molecule from its attachment to the ethylene-containing monomer unit. There are several types of cleavable linkers which are appropriate for such an application, many of which are readily available from commercial sources. Such linkers can be cleaved, for example, chemically, enzymatically, thermally or by exposure to light. For example, linkers containing disulfide bonds are sensitive to chemical cleavage (Mattson et al., Molecular Biology Reports 17:167–183 (1993)). Exposure of such a linker to a reducing agent such as β-mercaptoethanol or dithiothreitol, results in the cleavage of the disulfide bond. Linkers formed from either carbohydrates or peptides can be sensitive to cleavage by enzymatic means. Thermally sensitive and photocleavable linkers offer alternatives to the chemical or enzyme sensitive linkers, however, their use is not compatible with all methods of polymerization. For example, thermal induction of polymerization would result in cleavage of a linker sensitive to heat.

Covalent attachment of the nucleic acid or nucleic acid analogue to the first polymerizable ethylene-containing monomer group or linker can occur through any functional groups present on the nucleic acid, including the aromatic bases, sugars, and phosphates. Further, additional functional groups such as primary amines and thiols can easily be introduced during automated oligonucleotide synthesis using modified nucleotide or non-nucleotide phosphoramidite precursors. For most applications it will be preferable for the attachment to involve one end of the nucleic acid, to allow maximum accessibility of the immobilized nucleic acid to solution phase assay components. For hybridization applications, attachment can occur at either the 3' or 5' end. For polymerase extension assays, attachment must occur so that a free 3' hydroxyl group is available for priming.

Attachment can also involve functional groups on internal portions of the nucleic acid. Interior groups for coupling can be functional groups on the nucleotide bases, on the sugars, and on the phosphates. Additional chemical groups for internal attachment can be provided by chemically modifying the nucleotide bases, sugars, or phosphates. Such chemically modified positions could be incorporated during oligonucleotide synthesis or they could be added post-synthetically. Other groups for internal attachment can be provided by incorporating special non-nucleotide spacer phosphoramidites that carry the desired chemical functionality during oligonucleotide synthesis.

The first and second ethylene-containing monomer units can be either a polymerizable monosubstituted ethylene of general structure $CH_2$=CHX or a polymerizable unsymmetrically disubstituted ethylene of the general structure $CH_2$=CXY. For the first polymerizable ethylene-containing group the preferred structures are derivatives of acrylic acid, acrylamide, methacrylic acid, or methacrylamide.

The preferred structures for the second polymerizable ethylene-containing monomer units include, but are not limited to, acrylic acid, acrylamide, methacrylic acid, methacrylamide, N-vinyl pyrrolidone, methyl-methacrylate and acrylate esters such as 2-hydroxyethylmethacrylate. Numerous other useful polymerizable monomers units are specified in the literature (Sandler and Karo, *Polymer Synthesis* Vol. 1, Academic Press, Inc. (1992); Sandler and Karo, *Polymer Synthesis* Vol. 2, Academic Press, Inc. (1994)).

In one embodiment, the second polymerizable group of the form $CH_2$=CXY is attached to the surface of a formed material through either the X or Y group. An example of an appropriate second polymerizable ethylene-containing monomer unit is 3-(trimethoxysilyl)propyl methacrylate (Polysciences, Inc. Catalog, Warrington, Pa., pg. 22 (1996)). In the presence of water, the methoxy groups hydrolyze to yield silanol groups. These silanol groups condense with silanol groups on glass or silica surfaces to produce covalent siloxane linkages. As a result, the treated surface is coated with covalently bound methacrylate groups that can serve as second polymerizable ethylene-containing groups for copolymerization attachment.

The present invention also relates to methods for the production of a polymerized layer containing at least one nucleic acid molecule covalently attached. The polymerized layer itself can be formed into a variety of shapes, including but not limited to a flat planar sheet, a cylinder or a bead. The polymerized product can be formed through a molding process, for example. A preferred form, the bead, can be produced by introducing droplets of an aqueous polymerizing mixture into mineral oil or another appropriate immiscible organic solvent.

The method involves preparing a mixture comprising a first modified polymerizable ethylene-containing monomer unit, with a second unmodified polymerizable ethylene-containing monomer unit. To initiate the polymerization reaction between the first modified and second unmodified polymerizable ethylene-containing monomer units, a polymerizing reagent is added to the mixture. A cross-linking reagent can be added when the preferred polymerized layer is not a linear structure and additional strength and durability are required. The ratio of the first modified and second unmodified polymerizable ethylene-containing monomer units in the mixture can vary. Generally, it is important that the first polymerizable ethylene-containing monomer unit be present at a sufficiently high percentage such that the attached nucleic acid molecule exposed at the surface of the polymerized product is present at sufficiently high levels to facilitate the intended application. Routine experimentation may be necessary to determine optimum ratios for particular applications.

A wide variety of monomer types can be used and optimal conditions may differ widely according to monomer type. In a preferred embodiment for common hybridization and polymerase extension applications, an acrylamide gel containing 5–40% (weight monomer/volume) acrylamide, with N,N-methylene-bis-acrylamide added as a cross-linker (weight ratio of 20 acrylamide:1 bis-acrylamide) can be used. Adding between 0.1–100 µM of the nucleic acid probe conjugated to an appropriate first polymerizable ethylene-containing group to the polymerization mixture results in densities of approximately 0.1–100 fmoles nucleic acid probe per square millimeter of gel surface area. The mixture used to create a polymerized layer can be composed of more than one first modified and/or more than one second unmodified polymerizable ethylene-containing monomer units.

For many purposes, the preferred nucleic acid molecule will be an oligonucleotide produced using standard automated synthetic methods which utilize beta-cyanoethyl phosphoramidite substrates (Caruthers et al., *Methods in Enzymology* 154, 287–313 (1987)). For this reason, it would facilitate practice of the invention if one or more first polymerizable ethylene-containing monomer units could be added to the nucleic acid during automated synthesis of the nucleic acid molecule. Phosphoramidites which can be used for this purpose have the general formula a) or b) shown below:

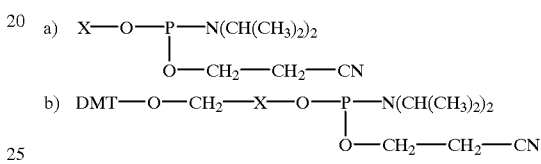

where DMT indicates a 4,4'-dimethoxytrityl group, and X contains either a first polymerizable ethylene-containing monomer unit, or a chemically protected version of a first polymerizable ethylene-containing monomer unit that can be deprotected by a suitable process. Compounds of type a) are useful for incorporating first polymerizable ethylene-containing monomer unit chemical groups at the 5' terminal position of the oligonucleotide. Compounds of type b) can be used for incorporating first polymerizable ethylene-containing monomer unit chemical groups anywhere within the oligonucleotide except at the residue which links the growing oligonucleotide to the solid phase support used for oligonucleotide synthesis. To place the first polymerizable ethylene-containing monomer unit at the 3' terminal positions of synthetic oligonucleotides, solid phase supports can be used which carry groups with the structure shown below in c):

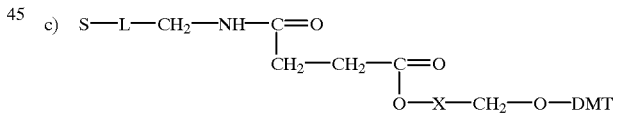

where S is a support material suitable for automated oligonucleotide synthesis, L is a linker group joining the support and the alkyl amine group, X is either a polymerizable ethylene-containing monomer unit, or a chemically protected version of a polymerizable ethylene-containing monomer unit which can be deprotected by a suitable process, and DMT is a 4,4'-dimethoxytrity group. Materials suitable for the synthetic supports described above include cross-linked polystyrene and controlled pore glass.

In the present invention, formation of a polymerized layer by chemical initiation includes copolymerization reactions that occur when a polymerizing reagent is added to a mixture consisting of a first modified polymerizable ethylene-containing monomer unit, and at least one second unmodified ethylene-containing monomer unit. Following addition of the polymerizing reagent to the mixture, a polymerized layer forms spontaneously. In a preferred embodiment, a polymerized layer is formed in this manner by creating a mixture containing a first polymerizable ethylene-containing monomer unit consisting of either N-(3-aminopropyl)-acrylamide or N-(3-aminopropyl)-methacrylamide, covalently attached to a nucleic acid by means of a linker, and a second polymerizable ethylene-containing monomer unit consisting of unmodified acrylamide monomers in solution. Polymerization can be initiated chemically by the addition of ammonium persulfate and N,N,N',N'- tetramethylethylenediamine (TEMED) to the polymerization reaction. In most preferred embodiments, it is desirable to include cross-linking reagents such as N,N-methylene-bis-acrylamide or ethylene glycol dimethacrylate in the polymerization mixture to improve the mechanical stability of the polymerized layer.

Polymerization reactions useful for the invention can proceed by radical or ionic chain-reaction mechanisms. For many applications, the radical chain-reaction mechanisms will be preferred since it occurs more efficiently in aqueous solution.

Initiation of polymerization can be accomplished using a number of means well known to those skilled in the art (Sandler and Karo, *Polymer Synthesis* Vol. 1, Academic Press, Inc. (1992); Sandler and Karo, *Polymer Synthesis* Vol. 2, Academic Press, Inc. (1994)). Initiation can be accomplished using chemical means, photochemical means, thermal means, or through the use of ionizing radiation. To initiate the polymerization reaction using light, a light source is directed into a solution containing the first modified and second unmodified polymerizable ethylene-containing monomer units. The use of light is described in greater detail in the Exemplification section which follows. Briefly, to the mixture containing the first modified and second unmodified polymerizable ethylene-containing monomer units, a photosensitive polymerizing reagent is added. This photosensitive polymerizing reagent is able to initiate the polymerization reaction when it is exposed to light. When the polymerization mixture is exposed to light capable of activating the photosensitive polymerizing reagent, the polymerization reaction is initiated and a polymerized layer is formed. Examples of useful photosensitive polymerization reagents include riboflavin, benzoin, benzoin ethyl ether, camphorquinone and benzophenone. Those skilled in the art are also familiar with other photosensitive polymerization reagents which would function appropriately. In some cases, where a polymerized layer of greater strength and durability is desired, a cross-linking reagent can be added to the mixture.

In another embodiment of the present invention, catalysis of polymerization occurs when heat is applied to a mixture containing the first modified and second unmodified polymerizable ethylene-containing monomer units and a polymerizing reagent. The polymerizing reagents that can be used to initiate polymerization following the application of heat include initiator compounds which decompose to free radicals upon application of heat. Examples of such initiators include dibenzoyl peroxide and bis-azo compounds such as 2,2'azobis(isobutyronitrile) which decompose productively when the polymerization mixture is warmed to temperatures in the range of 50–70° C.

Polymerization can also be initiated by exposing the mixture to a source of ionizing radiation such as gamma radiation. This treatment generates free radicals which can stimulate polymerization of many monomers without the need for chemical initiators or photosensitive reagents.

In a further aspect of the present invention, the polymerized layer containing a covalently attached nucleic acid molecule is itself covalently linked to a formed material. Preferred embodiments of the formed material include glass, plastic, metal, ceramic, or composite compounds such as carbon fiber. Each of these types of formed materials are capable of creating a covalent linkage to the polymerized layer following chemical modification of their surfaces such that polymerizable side chains are left exposed. Using glass, these polymerizable side chains can be created, for example, by treatment of the glass surface with an organosilane which contains polymerizable ethylene-containing chemical groups. An example of this type of organosilane is 3-(trimethoxysilyl)propyl methacrylate. In the presence of water, the methoxy groups hydrolyze to yield silanol groups. These silanols can condense with surface silanol groups on glass or silica surfaces, to produce covalent siloxane linkages. As a result, the treated surface is coated with covalently bound methacrylate groups that can serve as second unmodified polymerizable ethylene-containing monomer units for copolymerization attachment. Modified organosilane offers the advantage of spontaneous attachment to those glass surfaces it comes in contact with. The modified organosilane-based side chains attached to a glass surface can polymerize with both the first modified and unattached second unmodified polymerizable ethylene-containing monomer units during the creation of the polymerized layer.

Both glass and plastic offer the advantage that they are inexpensive and can be molded into a variety of shapes depending on the desired usage. For example, glass and plastic can be formed into beads, flat supports, tubes with or without an enclosed bottom, or long thin wire-like fibers. For use in the present invention, glass and plastic beads can be created in a variety of different sizes ranging from only a few microns to as large as a few millimeters. Glass can also be formed into optical fibers, nonplanar or planar sheets, cylinders, and containers for liquid samples.

In the Exemplification section which follows, glass is prepared such that the polymerized layer is covalently attached to the glass surface. Briefly, the glass is cleaned with nitric acid, washed with water and acetone, then air-dried. Next, the cleaned glass is soaked in a modified silane solution. As stated above, this results in the coating of the glass surface with covalently attached silane molecules which contain polymerizable ethylene-containing monomer units.

One type of formed glass that is effectively coated by this method is an optical fiber. Optical fibers can be used individually or in groups known as bundles. Briefly, a portion of a single optical fiber, or a bundle of optical fibers, is immersed in a mixture containing the polymerizing reagent, the first modified and the second unmodified polymerizable ethylene-containing monomer units. A cross-linking reagent can also be added to the mixture. Following immersion in the mixture, light is passed through a predetermined optical fiber or fibers. A polymerized layer covalently attaches to the silanized surface at the tip of the optical fiber or fibers through which light was passed. Those optical fibers present in the bundle through which light was not passed remain uncoated. Optical fibers not coated during the first polymerization reaction can be coated with a second polymerized layer containing a second nucleic acid distinct from the nucleic acid of the first polymerized layer, during a second polymerization reaction. By repeating the method described above, the tip of each optical fiber in the bundle can be coated with a unique nucleic acid molecule. Such bundles of optical fibers are useful for multi-analyte assays.

Another type of formed glass that can be covalently attached to a polymerized layer or multiple polymerized layers, each of which is covalently linked to a nucleic acid molecule, is a slide or coverslip. The glass slide or coverslip is first treated with modified silane as described above. The polymerization reaction can be initiated using either chemical catalysis, light-induced catalysis or thermally-induced catalysis. The polymerizing reagent added to the mixture will depend on the method of polymerization. A cross-linking reagent can also be added.

Glass slides and coverslips are also useful for multi-analyte assays in which the sample is applied to a surface containing an array of immobilized nucleic acid probes. The present invention is useful for these inventions since it is easy to pipette discrete noncontiguous spots of polymerization mixtures onto the surface of an appropriately treated glass sheet, each polymerization mixture containing a unique hybridization probe. Following polymerization, each spot will contain a single hybridization probe which can be identified from its position within the array. Pipetting can be performed manually or robotically. Sophisticated imaging techniques can be used to analyze hybridization of fluorescently labeled samples to such arrays as used in high throughput screening methods.

Plastic is another formed material which can be treated such that reactive side chains are created on the surface. These surface reactive side chains are covalently linked to polymerizable ethylene-containing monomer units. As described for glass above, when the reactive side chains are exposed to a mixture containing the polymerizing reagent, the first modified and the second unattached, unmodified polymerizable ethylene-containing monomer units, a polymerization reaction ensues which coats the plastic with a polymerized layer which is covalently attached. A wide variety of shaped plastic materials in common usage in connection with molecular biological techniques can be modified in this manner. Examples include multi-welled plates, flat sheets, tubes with or without enclosed bottoms (e.g., test tube, microfuge tube and a cylindrical tube open at both ends), beads, and optical fibers. The test tube and microfuge tube both are capable of holding a liquid sample while the pipe-like tube can have a sample put through it.

Methods for coating a formed material other than glass or plastic with a polymerized layer are similar to those described above. Briefly, the formed material is treated such that reactive side chains are created which can be covalently linked to polymerizable ethylene-containing monomer units. The formed material is placed in a mixture containing the polymerizing reagent, the first modified and second unmodified polymerizable ethylene-containing monomer units. During polymerization, the reactive side chains on the formed material will polymerize with the components of the mixture to form a polymerized layer which is covalently attached to the formed material. A cross-linking reagent can be added to the mixture depending on the desired structure of the polymerized layer.

The formed material coated with the polymerized layer containing the covalently attached nucleic acid molecules or the polymerized layers themselves can be used for many different experimental and diagnostic assays. For example, glass or plastic beads that are coated with the polymerized layer can be placed in a column to purify and isolate a nucleic acid of interest. A solution containing nucleic acids is applied to the column under appropriate conditions such that those nucleic acids present in the sample which are capable of hybridizing to the nucleic acid covalently attached to the polymerized layer, bind to the covalently attached nucleic acid. The bound nucleic acids are then eluted off the beads for further study.

Glass slides, coverslips and optical fiber bundles containing more than one unique nucleic acid sequence which are covalently linked to a polymerized layer which itself is covalently attached to the glass surface can be used for high throughput assays. These assays are effective in screening experimental or diagnostic samples believed to contain a single or multiple nucleic acids of interest. In one embodiment, if the sequences of each nucleic acid covalently attached to the polymerized layer is known, these formed glass materials can be used to identify an individual or group of nucleic acids of interest by at least a portion of their sequence. By visualizing the specific polymerized layer the sample nucleic acids bound, identification of the sample nucleic acid, and at least a partial sequence can be accomplished. In a second embodiment, these formed glass materials can be used to identify mutations in sample nucleic acid molecules. In this case, nucleic acid molecules of known sequence are covalently attached to the formed glass structure by means of the polymerized layer. Each of these nucleic acid molecules contains individual or multiple base pair changes in the nucleic acid sequence from that of the wild-type DNA sequence. Identification of the mutant nucleic acid in the sample is determined by which covalently attached nucleic acid it specifically hybridizes to.

EXEMPLIFICATION

The following example demonstrates a simple and efficient method for attaching a DNA molecule to a solid support. Although an oligonucleotide is exemplified, a variety of different types of nucleic acid molecules can be used. In the present example, the oligonucleotide was chemically modified through the attachment of an aminoacrylate group. Following attachment of the aminoacrylate group, the modified DNA molecule was copolymerized with acrylamide to form an acrylamide gel layer on a solid support.

Modification of a DNA Molecule

The method used to modify an oligonucleotide for use in connection with the present invention involves attaching aminoacrylate groups to the 5' end of the oligonucleotide. In the present example, oligonucleotides were modified with N-(3-aminopropyl)-acrylamide which was coupled to the 5' terminal phosphate of the DNA molecule using carbodiimide. As described below, when a solution containing the modified oligonucleotides and an acrylamide gel solution is treated with a chemical polymerization initiators, the copolymerization reaction occurs with the subsequent formation of acrylamide gels.

Copolymerization of 5'-acrylate-modified Oligonucleotides into Acrylamide Gel Matrixes To demonstrate that oligonucleotides were covalently attached to the acrylamide gel, 5'-aminoacrylate 13B oligonucleotides (5'-$PO_4$- TTTTTTTTCGGGATCCCAGGC-CCGGGAACGTAT TCAC-3', SEQ ID No:1) or unmodified 13B oligonucleotides were copolymerized into 8% (wt/vol) total acrylamide (10:1 weight ratio acrylamide/N,N' methylene bis acrylamide) plugs (50 µl) with ammonium persulfate and TEMED. After polymerization, the plugs were placed in the wells of a 20% acrylamide gel and electrophoresed to remove unattached oligonucleotides from the plugs. Following electrophoresis, the plugs and 20% acrylamide gel were stained with SYBR green II (Molecular Probes, Eugene, Oreg.) and photographed under UV illumination. Virtually all of the modified oligonucleotide was trapped in the acrylamide gel plug, as judged by the staining intensity of the modified oligonucleotide gel plug. In contrast, most of the unmodified oligonucleotide entered the 20% acrylamide gel.

Photochemical Probe Attachment by Copolymerization

Photochemical probe attachment by copolymerization to a glass surface is also possible using the modified oligonucleotides. This method was accomplished by mixing aminoacrylate-modified oligonucleotides with an acrylamide gel solution containing riboflavin. One glass surface that can be successfully coated in this manner is a glass optical fiber. Prior to exposure to the solution containing the modified oligonucleotide and the acrylamide gel solution containing riboflavin, the optical fiber was polished and silanized with an acrylic silane (3-methacryloxypropyltriethoxysilane). The silanized tip of the optical fiber was then immersed in the gel solutions while the opposite end of the fiber was illuminated with a light source. A small amount of gel containing immobilized oligonucleotide was formed on the fiber tip.

Hybridization analysis showed an extremely high level of immobilized oligonucleotide attached to the acrylamide gel coating the fiber tip. More specifically, the experimental protocol involved hybridizing the coated fiber tips to 0.1 $\mu$M complementary $^{32}$P-labeled oligonucleotide probe 13B-C (5'-GTGAATACGTTCCCGGGCCT-3; SEQ ID No2), which was 3' end-labeled with terminal transferase and $\alpha$-$^{32}$P-labeled dCTP. In addition, coated tips were hybridized to complementary probe in the presence of a 100-fold excess of unlabeled 13B, and in the presence of a 100-fold excess of unlabeled non-homologous probe Bglo+-c (5'-TGAACGTGGATGAAGTTG; SEQ ID No.3). From the results of these various hybridizations, the quantity of immobilized oligonucleotide present on the coated tip could be deduced. The specific activity of the probe was ~12,000 cpm/pmole. Approximately 0.15 pmoles of the 5'-aminoacrylate 13B $^{32}$P-labeled probe were immobilized on the fiber tips, which corresponds to 190 fmoles of oligonucleotide present for every mm$^2$ of tip surface area coated with the modified oligonucleotide. Hybridization analysis of fibers which were coated with unmodified acrylamide gel solution containing oligonucleotides in place of the modified oligonucleotides showed no immobilized probe present on the tip.

Other glass surfaces that can be coated by copolymerization attachment of a modified oligonucleotide include a flat glass support (e.g., coverslip or glass slide). Coverslips were spotted with an acrylamide gel containing either a modified oligonucleotide or an unmodified oligonucleotide. Coverslips were spotted such that the mixtures using unmodified oligonucleotides were placed side by side with the modified oligonucleotide spots. Spotted coverslips were then hybridized to a $^{32}$P-labeled 13B-C oligonucleotide probe (0.1 $\mu$M) present in hybridization buffer (TE buffer with 0.2M NaCl and 0.1% SDS) for 15 minutes at room temperature. After hybridization, the coverslips were washed with three changes (10 ml per change) of hybridization buffer without probe, air dried, and exposed to x-ray film. The resulting autoradiogram showed that hybridization only occurred within spots on the coverslips which were produced with the 5'-aminoacrylate-modified oligonucleotide mixture. No hybridization was visible within spots on the coverslips which were produced with the unmodified oligonucleotide mixture. This showed that successful hybridization to an acrylamide gel spot on a coverslip was specifically mediated by copolymerization of the 5'-aminoacrylate group with acrylamide to form the acrylamide gel.

The data presented herein demonstrate that gel-mediated attachment is simple and efficient. Photochemical activation of polymerization to a glass surface has the additional benefit that light-directed methods can be used to create precise patterns or arrays of oligonucleotides or other DNA molecules onto a glass surface. These photochemical processes are useful for the automated manufacture of devices containing arrays of immobilized DNA molecules.

MATERIALS AND METHODS

Attachment of Terminal Acrylate Group to Oligonucleotides

A mixture containing 0.25M N-(3-aminopropyl) methacrylamide-HCl (Polysciences), 0.1M 1-methyl-imidazole (pH 7.0), 0.1M 1-ethyl-3-(3-dimethylaminopropyl) carbodiimide-HCl (EDC), and 30 to 50 $\mu$M of 5'-phosphorylated DNA oligonucleotide 13B (5'-PO$^4$-TTTTTTTTTCGGGATCCCAGGCCCGGGAACGTAT TCAC-3'; SEQ ID No. 1) was incubated at 50° C. for 1 hour in a final reaction volume of 100 $\mu$l. Following the reaction, the reaction mixture was diluted 10-fold with a solution containing 0.2M NaOH/1mM EDTA, and run over a Sephadex G-25 column (NAP10 disposable columns, Pharmacia), and equilibrated in 0.1M NaOH/ 1mM EDTA. The excluded fraction was collected, concentrated and exchanged into TE buffer (10 mM Tris-HCl, pH 8.3, 1 mM EDTA) by several cycles of centrifugal ultrafiltration and dilution (Microcon 3, Amicon).

Photochemical Attachment of Primers to Optical Fibers

The polished ends of silica optical fibers (1 mm diameter) were cleaned by soaking in 10% aqueous nitric acid for two hours. The fibers were rinsed with water and acetone, and then air-dried. The fiber tips were then soaked in 10% 3-methacryloxypropyltrimethoxysilane in acetone (v/v) for one hour after which time the tips were washed in acetone and air dried.

To coat the silanized tips with oligonucleotide, the tips were immersed in 20 $\mu$l solutions of 8% (wt/v) acrylamide (17:1 weight ratio, acrylamide:bis-acrylamide, in 0.1M phosphate buffer, pH 6.8) containing 1 $\mu$M 5'-aminoacrylate primer 13B (modified oligonucleotide samples) or 1 $\mu$M unmodified 5'-phosphate oligonucleotide 13B (unmodified oligonucleotide samples). Riboflavin was added to a final concentration of 0.0006% wt/vol, and light from a 100 W halogen lamp was passed through the fiber for 5 minutes. Following irradiation, the coated fiber tips were immersed in an agarose minigel box containing an acrylamide gel running buffer composed of a 10 mM Tris-HCl pH 8.0 and 1 mM EDTA solution, and electrophoresed for 30 minutes at 100 v/cm to remove non-immobilized oligonucleotide.

Copolymerization Attachment to Create Hybridization Arrays

A borosilicate coverslip was cleaned by soaking in 10% (v/v) aqueous nitric acid for two hours. A glass slide can also be used. The coverslip was rinsed with water and acetone, and then air-dried. Subsequently, the coverslip was soaked in 10% 3-methacryloxypropyltrimethoxysilane in acetone (v/v) for one hour, at which time the coverslip was rinsed in several changes of acetone and air dried.

Two copolymerization mixtures were prepared. One contained 5'-aminoacrylate modified 13B oligonucleotide at 1 $\mu$M. The other contained unmodified (5'-phosphate) 13B oligonucleotide at 1 $\mu$M. Both mixtures contained 20% (wt/vol) acrylamide (19:1 weight ratio, acrylamide:bis-acrylamide), 45 mM Tris-borate pH 8.3, 1mM EDTA. Polymerization was catalyzed by addition of TEMED to 0.14% (v/v) and ammonium persulfate to 0.08% (wt/v). Immediately after adding the required catalysts, four 0.25 $\mu$l spots of each mixture were pipetted by hand onto one of the silanized coverslips to form a 2×4 spot array. After polymerization for 15 minutes at room temperature, the coverslip was washed with deionized water, and placed in an agarose gel electrophoresis chamber filled with an acrylamide gel running buffer consisting of a 10 mM Tris-HCl pH 8.3, 1 mM EDTA (TE) solution. The slide was electrophoresed (10V/cm) for 20 minutes at room temperature to remove unbound oligonucleotides.

Copolymerization Attachment of Oligonucleotides to a Polystyrene Surface

The wells of a polystyrene microtiter dish are treated with potassium permanganate dissolved in 1.2N sulfuric acid (50 mg $KMnO^4$ per ml 1.2N $H_2SO_4$) for 30 minutes at 60° C. to introduce carboxyl groups on the polystyrene surface. The wells are washed with 6N hydrochloric acid to remove the permanganate residue, followed by water washes to remove the acid. Surface methacrylate groups are introduced by treating the wells at 50° C. for 1 hour with an aqueous solution containing 0.1M imidazole buffer pH 6.0, 0.1M 1-ethyl-3-(3-dimethylaminopropyl) carbodilmide-HCl (EDC), and 0.1M N-(3-aminopropyl)methacrylamide-HCl (Polysciences, Warrington, Pa.). The wells are washed thoroughly with water and air dried. Copolymerization attachment of the aminoacrylate-modified 13B oligonucleotide to the bottom surface of the carboxylated microwells is performed using the same gel mixture as used in the previous example. Fifty microliters of gel mixture were added to coat the bottom of each well.

reactant, said formed material being covalently linked through said polymerizable groups to a polymerizable complex comprising a nucleic acid molecule which is derivatized by attachment to a first monomer unit which contains a polymerizable ethylene group, thereby forming a nucleic acid-containing polymerized layer on said surface that optionally also comprises at least one second monomer unit which, in unreacted form, contains a polymerizable ethylene group and is not attached to a solid support.

2. An article of manufacture, as claimed in claim 1, wherein said polymerized layer includes said at least one second monomer unit.

3. An article of manufacture, as claimed in claim 2, wherein said polymerized layer is cross-linked with a cross-linking reagent.

4. An article of manufacture, as claimed in claim 3, wherein said cross-linking reagent comprises a multifunctional monomer unit containing at least two polymerizable ethylene-containing monomer units.

5. An article of manufacture, as claimed in claim 4, wherein said cross-linking reagent is selected from the group consisting of bis-acrylates, N,N'-methylene(bis)acrylamide and ethylene glycol dimethacrylate.

6. An article of manufacture, as claimed in claim 2, wherein said formed material comprises a substance selected from the group consisting of glass, silicon, metal, ceramic and plastic.

What is claimed is:

1. An article of manufacture comprising a formed material having a surface at least a portion of said surface bearing polymerizable groups thereon, said polymerizable groups being reactive with at least one ethylene group-containing 7. An article of manufacture, as claimed in claim 2, wherein said formed material is in the form of a bead.

8. An article of manufacture, as claimed in claim 2, wherein said formed material is in the form of a flat, planar sheet.

9. An article of manufacture, as claimed in claim 2, wherein said formed material is in the form of a liquid container or a part of a liquid container.

10. An article of manufacture, as claimed in claim 2, wherein said formed material is in cylindrical form.

11. An article of manufacture, as claimed in claim 2, wherein said formed material is in the form of a tube open at each end.

12. An article of manufacture, as claimed in claim 2, wherein said nucleic acid-containing polymerized layer is disposed in discrete noncontiguous spots on the surface of said formed material, each spot comprising a nucleic acid molecule which is different from that of each other spot.

13. An article of manufacture comprising at least one optical fiber having a surface, at least a portion of said surface bearing polymerizable groups thereon, said polymerizable groups being reactive with at least one ethylene group-containing reactant, said at least one optical fiber being covalently linked through said polymerizable groups to a polymerizable complex comprising a nucleic acid molecule which is derivatized by attachment to a first monomer unit which contains a polymerizable ethylene group, thereby forming a nucleic acid-containing polymerized layer on said surface, said polymerized layer also comprising at least one second monomer unit which, in unreached form, contains a polymerizable ethylene group and is not attached to a solid support.

14. An article of manufacture, as claimed in claim 13, wherein said at least one optical fiber bears, as said polymerizable groups, ethylene moieties on a light transmitting surface of said optical fiber, and said nucleic acid-containing polymerized layer is covalently coupled to said ethylene moieties on said light transmitting surface.

15. An article of manufacture as claimed in claim 13, further comprising a bundle of optical fibers.

16. An article of manufacture as claimed in claim 15, wherein each optical fiber in said bundle has, as said polymerizable group, ethylene moieties on a light transmitting surface of said fiber, said nucleic acid-containing polymerized layer being covalently linked to said ethylene moieties on said light transmitting surface, and the nucleic acid-containing polymerized layer which is present on each optical fiber of said bundle comprises a different nucleic acid from that on each other optical fiber in said bundle.

17. An article of manufacture, as claimed in claim 2, wherein the nucleic acid molecule is a deoxyribonucleic acid.

18. An article of manufacture, as claimed in claim 17, wherein the deoxyribonucleic acid molecule is an oligonucleotide.

19. An article of manufacture, as claimed in claim 2, wherein the nucleic acid is a ribonucleic acid.

20. An article of manufacture, as claimed in claim 2, wherein the nucleic acid is a nucleic acid analog having a modified backbone holding DNA bases at the proper distance to facilitate hybridization with complementary single stranded DNA and RNA molecules.

21. An article of manufacture, as claimed in claim 20, wherein the nucleic acid analog is a peptide nucleic acid.

22. An article of manufacture, as claimed in claim 2, wherein said nucleic acid molecule is derivatized by attachment to at least one water soluble, first monomer unit selected from the group consisting of acrylamide, methacrylamide, acrylic acid, methacrylic acid and derivatives thereof.

23. An article of manufacture, as claimed in claim 2, wherein said at least one second monomer unit is selected from the group consisting of acrylic acid, acrylamide, methacrylic acid, methacrylamide, N-vinyl pyrrolidone, methylmethacrylate and 2-hydroxyethylmethacrylate.

24. A method for producing an article of manufacture comprising a formed material having a surface which is covalently linked to a nucleic acid-containing polymerized layer, the method comprising:
   a. providing said formed material, at least a portion of the surface of which bears polymerizable groups thereon, said polymerizable groups being reactive with at least one ethylene group-containing reactant; and
   b. forming a polymerization mixture by contacting said formed material with at least one polymerizable reactant, under conditions appropriate for polymerization, said at least one polymerizable reactant comprising:
      (i) a polymerizable complex comprising a nucleic acid molecule which is derivatized by attachment to a first monomer unit which contains a polymerizable ethylene group, said polymerizable complex being capable of polymerization in the presence of another monomer unit containing a polymerizable ethylene group under appropriate conditions; and
      (ii) optionally, at least one second monomer unit which contains a polymerizable ethylene group and which is not attached to a solid support.

25. A method, as claimed in claim 24, wherein the polymerizable groups are created on the surface of said formed material by chemical modification of said surface.

26. A method, as claimed in claim 25, wherein said at least one polymerizable reactant includes said polymerizable complex and said at least one second monomer unit.

27. A method as claimed in claim 24, wherein said polymerizable complex comprises a nucleic acid indirectly attached to said first polymerizable monomer unit through a chemical linker group.

28. A method, as claimed in claim 24, wherein said nucleic acid molecule is derivatized by attachment to at least one water soluble, first monomer unit selected from the group consisting of acrylamide, methacrylamide, acrylic acid methacrylic acid and derivatives thereof.

29. A method, as claimed in claim 24, wherein said at least one second monomer unit is selected from the group consisting of acrylic acid, acrylamide, methacrylic acid, methacrylamide, N-vinyl pyrrolidone, methyl-methacrylate and 2-hydroxyethylmethacrylate.

30. A method as claimed in claim 24, wherein said polymerization mixture further comprises a cross-linking agent.

31. A method as claimed in claim 30, wherein said cross-linking agent is selected from the group consisting of bis-acrylates, N,N'-methylene(bis)acrylamide and ethylene glycol dimethacrylate.

32. A method for producing an article of manufacture comprising at least one optical fiber having a surface which is covalently linked to a nucleic acid-containing polymerized layer, the method comprising:
   a. providing said at least one optical fiber, at least a portion of the surface of which bears polymerizable groups thereon, said polymerizable groups being reactive with at least one ethylene group-containing reactant; and
   b. forming a polymerization mixture by contacting said at least one optical fiber with at least one polymerizable reactant, under conditions appropriate for polymerization, said at least one polymerizable reactant comprising:

(i) a polymerizable complex comprising a nucleic acid molecule which is derivatized by attachment to a first monomer unit which contains a polymerizable ethylene group, said polymerizable complex being capable of polymerization in the presence of another monomer unit containing a polymerizable ethylene group under appropriate conditions; and
(ii) optionally, at least one second monomer unit which contains a polymerizable ethylene group and which is not attached to a solid support, said polymerization mixture further comprises a photosensitive polymerizing reagent and said polymerization is initiated by exposing said polymerization mixture to light capable of activating said photosensitive polymerizing reagent.

33. A method as claimed in claim 32, wherein said photosensitive polymerizing reagent is selected from the group consisting of riboflavin, benzoin, benzoin ethyl ether, camphorquinone and benzophenone.

34. A method as claimed in claim 33, wherein said polymerization mixture further comprises a cross-linking reagent.

35. A method as claimed in claim 34, wherein said cross-linking agent is selected from the group consisting of bis-acrylates, N,N'-methylene(bis)acrylamide and ethylene glycol dimethylacrylate.

* * * * *

UNITED STATES PATENT AND TRADEMARK OFFICE
CERTIFICATE OF CORRECTION

PATENT NO. : 6,692,912 B1
DATED : February 17, 2004
INVENTOR(S) : Boles et al.

It is certified that error appears in the above-identified patent and that said Letters Patent is hereby corrected as shown below:

Title page,
Item [56], References Cited, U.S. PATENT DOCUMENTS, reads "5,453,461 A 9/1995 Helliger et al. 525/329.4" and should read -- 5,453,461 A 9/1995 Heiliger et al. 525/329.4 --.
FOREIGN PATENT DOCUMENTS, reads "JP 06121698 6/1994 C12Q/1/68" and should read -- WO 8910977 11/1989 C12Q/1/68 --.
OTHER PUBLICATIONS, reads "S. Nagahara et al., Hydrogel formation via hybridization oligonucleotides derivatized in water-soluble vinyl polymers"; " and should read -- S. Nagahara et al., Hydrogel formation via hybridization of oligonucleotides derivatized in water-soluble vinyl polymers"; --.

Column 2,
Line 15, reads "Each of the methods disclosed above have specific limitations." and should read -- Each of the methods disclosed above has specific limitations. --.

Column 3,
Lines 42-43 and 51-52, read "... structure CH2==CHX, and unsymmetrically (1,1-) disubstituted ethylenes of the general structure CH2==CXY." and should read -- ... structure $CH_2$==CHX, and unsymmetrically (1,1-) disubstituted ethylenes of the general structure $CH_2$==CXY. --.
Lines 55 and 66, read "... covalently to a nucleic acid-containing a polymerized coating..." and should read -- ... ... covalently to a nucleic acid containing a polymerized coating... --.

Column 4,
Lines 10-11, read "... CH2==CHX, and unsymmetrically (1,1-) disubstituted ethylenes of the general structure CH2==CXY." and should read -- ... $CH_2$==CHX, and unsymmetrically (1,1-) disubstituted ethylenes of the general structure $CH_2$==CXY. --.

Column 6,
Line 56, reads "...17:4769-4782 (1989). It is also possible to synthesize..." and should read -- ...17:4769-4782 (1989)). It is also possible to synthesize... --.

Column 12,
Lines 4-5, read "...carbon fiber. Each of these types of formed materials are capable of creating a covalent..." and should read -- ...carbon fiber. Each of these types of formed materials is capable of creating a covalent... --.

Column 14,
Line 44, reads "...treated with a chemical polymerization initiators, the..." and should read -- ...treated with chemical polymerization initiators, the... --.

UNITED STATES PATENT AND TRADEMARK OFFICE
CERTIFICATE OF CORRECTION

PATENT NO.     : 6,692,912 B1
DATED          : February 17, 2004
INVENTOR(S)    : Boles et al.

It is certified that error appears in the above-identified patent and that said Letters Patent is hereby corrected as shown below:

Column 15,
Line 22, reads "... (5'-GTGAATACGTTCCCGGGCCT-3; SEQ ID No2), ..." and should read -- ... (5'-GTGAATACGTTCCCGGGCCT-3; SEQ ID No: 2), ... --.
Line 28, reads "... TGAACGTGGATGAAGTTG; SEQ ID No.3), ..." and should read -- ...TGAACGTGGATGAAGTTG; SEQ ID No: 3), ... --.

Column 16,
Lines 11-12, read "... 50 $\mu$M of 5'phosphorylated DNA oligonucleotide 13B (5'-PO$^4$ - ..." and should read -- ... 50 $\mu$M of 5'phosphorylated DNA oligonucleotide 13B (5'-PO$_4$ - ... --.
Line 14, reads "... TCAC-3'; SEQ ID No. 1) was incubated at 50° C. for 1 hour ..." and should read -- ... TCAC-3'; SEQ ID No: 1) was incubated at 50° C. for 1 hour ... --.

Column 17,
Line 10, reads "... mg KMnO$^4$ per ml 1.2N H$_2$SO$_4$) for 30 minutes ..." and should read -- mg KMnO$_4$ per ml 1.2N H$_2$SO$_4$) for 30 minutes ... --.

Column 19,
Lines 26-27, read "... comprising at least one second monomer unit which, in unreached form, contains a polymerizable ethylene group ..." and should read -- ... comprising at least one second monomer unit which, in unreacted form, contains a polymerizable ethylene group... --.

Column 20,
Lines 40-41, read "... groups consisting of acrylamide, methacrylamide, acrylic acid methacrylic acid and derivatives thereof." and should read -- ... groups consisting of acrylamide, methacrylamide, acrylic acid, methacrylic acid and derivatives thereof. --.

Signed and Sealed this

Fourth Day of October, 2005

JON W. DUDAS
*Director of the United States Patent and Trademark Office*